United States Patent [19]

Wu

[11] Patent Number: 4,907,577
[45] Date of Patent: Mar. 13, 1990

[54] SPINAL TRANSPEDICLE DRILL JIG

[76] Inventor: Shing-Sheng Wu, 2 Fl., No. 640-2, Ting Chow Rd., Taipei, Taiwan

[21] Appl. No.: 331,818

[22] Filed: Apr. 3, 1989

[51] Int. Cl.⁴ .............................................. A16F 2/46
[52] U.S. Cl. ...................................... 606/87; 606/73; 606/80; 606/96; 606/104
[58] Field of Search .......... 128/92 VY, 92 V, 92 VZ, 128/92 VD, 92 VT, 92 YM, 92 YJ, 92 YF, 92 VV, 92 VW, 92 R, 92 ZY, 92 ZW, 92 ZK, 92 YP, 92 YL, 92 ZZ, 92 Z; 269/322, 323, 324

[56] References Cited

U.S. PATENT DOCUMENTS

| 2,593,624 | 4/1952 | Stevens | 128/69 |
| 3,865,105 | 2/1975 | Lode | 128/92 YM |
| 3,961,854 | 6/1976 | Jaquet | 128/92 ZW |
| 4,220,146 | 9/1980 | Cloutier | 128/92 VW |
| 4,245,638 | 1/1981 | Lebect | 128/92 VZ |
| 4,308,863 | 1/1982 | Fischer | 128/92 ZZ |
| 4,662,365 | 5/1987 | Gotzen | 128/92 Z |
| 4,696,293 | 9/1987 | Ciullo | 128/92 Z |

FOREIGN PATENT DOCUMENTS

2159680 12/1985 United Kingdom .......... 128/92 VY

Primary Examiner—Robert A. Hafer
Assistant Examiner—Michael Brown
Attorney, Agent, or Firm—Kolisch, Hartwell & Dickinson

[57] ABSTRACT

A spinal transpedicle drill jig adapted for providing a safe route for drilling, including an I-shaped body, a guiding base and a positioning base. The jig provides a precise location for drilling to prevent deviation of the drilling direction so as to prevent injury during surgery to the nerve root or spinal cord.

12 Claims, 11 Drawing Sheets

SPINAL TRANSPEDICLE DRILL JIG

BACKGROUND OF THE INVENTION

The present invention relates to a spinal transpedicle drill jig, and more particularly to such a drill jig adapted for providing a passage for a transpedicle screw to pass through so as to provide a safer and easier way during operation.

Heretofore, fractures or dislocation of spine were often treated by utilizing Harrington Hooks on the lamina or Luque Sublaminal Wiring to remedy vertebral bodies. However, in this way, it was necessary to fit at least five vertebral bodies, so as to easily cause some side-effects such as backache and the like.

Thus, those skilled in this art have found that to fix the vertebral bodies by means of transpedicle screws reduces the precentage of side-effects occurring. It has been proved from biomechanical study that fixing vertebral bodies by transpedicle screws provides greater stability than conventional hooking and wiring. Broadly speaking, the more deeply the screws are drilled in the pedicle, the more stable the vertebral bodies will be fixed. However, the location of drilling and the angle between the central axis of the vertebral bodies and the direction of drilling play important roles. Slight deviations of drilling direction could injure the nerve roots or spinal cord. Therefore, methods to prevent nerve roots and spinal cords from being hurt and to stabilize using transpedicle screws to fix the vertebral bodies are important factors in clinical operation.

A number of dissections on thoracic spine and lumbar spine, the fact of that the crossing point of the line along the lateral border of the superior articular process and the line along the center of the transverse process is the preferred location for drilling has been established. Also, the preferable angle measured from the thoracic spine between the axis of the transpedicle and the axis of the vertebral bodies has been statistically determined to be 10 degrees and the angle measured from lumbar spine is preferably 15 degrees, as analyzed on the transverse plane.

SUMMARY OF THE INVENTION

In order to mitigate and/or obviate the above-mentioned drawbacks in the manner set forth in the detailed description of the preferred embodiment, the primary objective of the present invention is to provide a spinal transpedicle drill jig which facilitates drilling to fix vertebral bodies.

Another objective of the present invention is to provide a spinal transpedicle drill jig adapted for precisely drilling while operating.

A further objective of the present invention is to provide a spinal transpedicle drill jig which provides a precise route for the transpedicle screw to pass through so as to prevent damage to hurt the nerve roots or the spinal cord.

Another objective of the present invention is to provide a spinal transpedicle drill jig which can be used to define a passage from 10 to 15 degrees converging to the central axis of the vertebral body on the transverse plan.

These and additional objectives, if not set forth specifically herein, will be readily apparent to those skilled in the art from the detailed description provided hereinbelow, with appropriate reference to the accompanying drawing.

DETAILED DESCRIPTION OF THE PREFERRED EMBODIMENT

Figure 1:
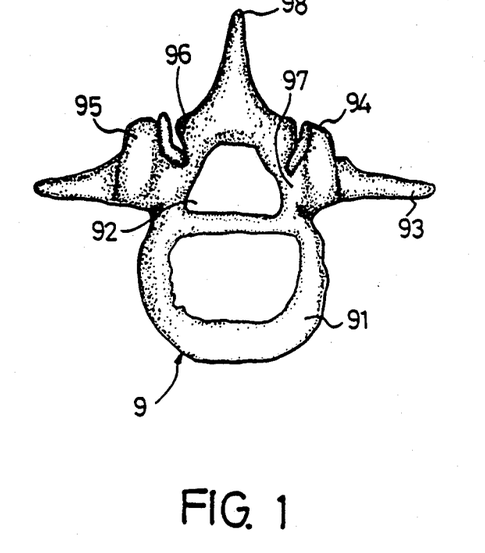
FIG. 1 is a top plan view of a vertebral body.
Figure 2:
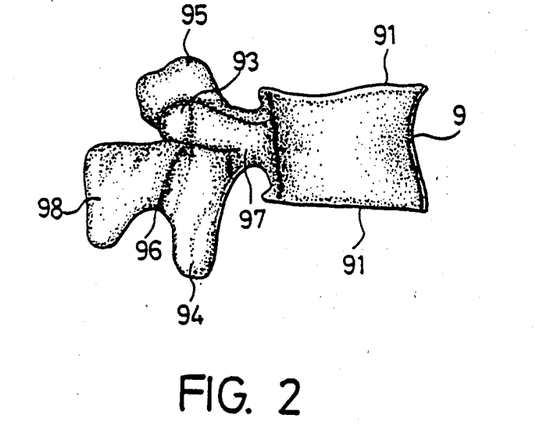
FIG. 2 is a side elevational view of the vertebral body of FIG. 1.

As can be seen in FIG. 1, a normal vertebral body 9 has an end plate 91, a spinal canal 92 with a spinal cord therein, a transverse process 93 which is located at each side of the vertebral body 9, an inferior articular process 94 and superior articular process 95 which are adjacent to each transverse process 93 respectively, a pedicle 97 located in each side, a lamina 96 behind each pedicle 97 and a spinal process 98. Referring to FIG. 2, the abutment of inferior articular process 94 (or superior articular process 95) and the transverse process 93 is the suitable location for drilling.

One embodiment of a spinal transpedicle drill jig according to the present invention is shown in FIGS. 3-7. The spinal transpedicle drill jig adapted for providing a precise passage for a screw to pass through further to fix the vertebral body comprises an I-shaped body 1, a pair of guiding bases 2 and a pair of positioning bases 3.

Figure 3:
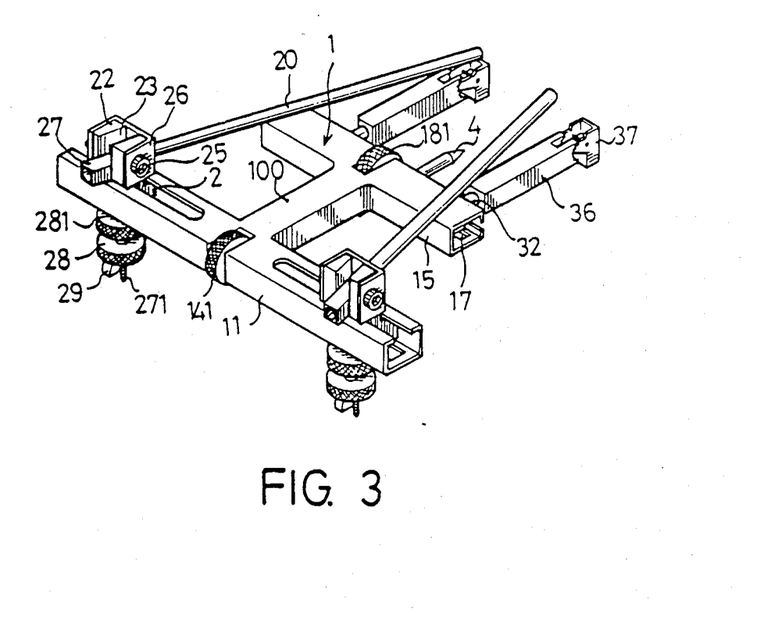
FIG. 3 is a perspective view of a first embodiment of a spinal transpedicle drill jig in accordance with the present invention.
Figure 4:
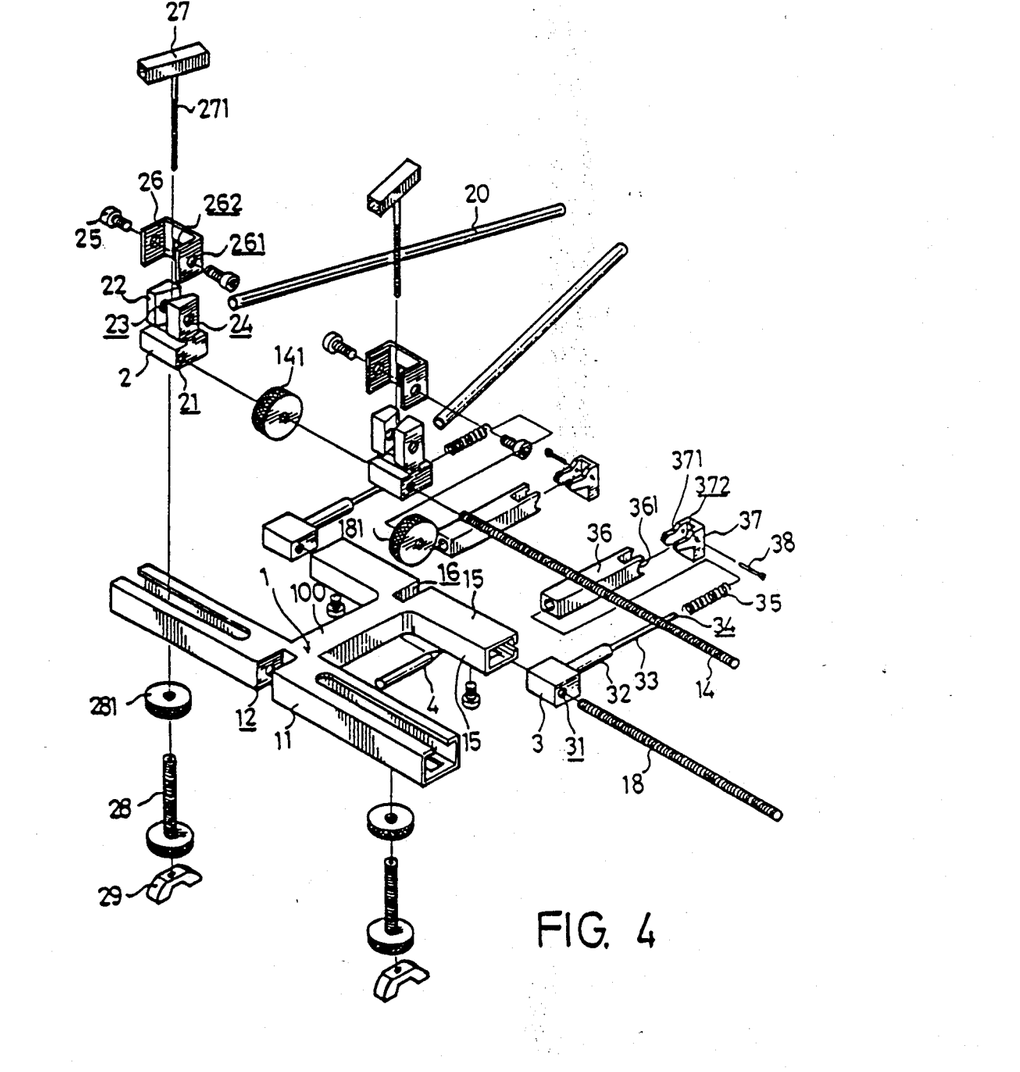
FIG. 4 is an exploded view of the spinal transpedicle drill jig of FIG. 3.

The I-shaped body 1 is formed with a pair of front rails 15 and a pair of rear rails 11. Each rear rail 11 and each front rail 15 are symmetrical about a central connecting portion 100. A first adjuster receiving means 12 is provided between each rear rail 11 for receiving a first width adjuster 141. A second adjuster receiving means 16 is provided between each front rail 15 for receiving a second width adjuster 181. Each guiding base 2 is slidable and securable in respective rear rail 11 and is engageable with a sleeve means 27 integral with a threaded end 271 thereunder. Likewise, each positioning base 3 is slidable and securable in a respective front rail 15 and is engageable with a respective positioning arm 36.

Each of the pair of guiding bases 2 has two clamping blocks 22 at an upper end thereof to form a tolerance 23 and a threaded hole 21 extending lengthwise through a lower end thereof. Each of clamping blocks 22 has a threaded aperture 24 thereon and two holes 261 formed on a U-shaped plate 26 align with the apertures 24 respectively so as to secure the U-shaped plate 26 on the clamping blocks 22 by mounting two screws 26. An opening 262 is formed on the U-shaped plate 26 in the middle portion for receipt of the sleeve means 27 therethrough. Further, the sleeve means 27 is engageable with a guiding sleeve 20 and secure the guiding sleeve 20 on the rear rail 11 by means of the threaded end 271 of the sleeve means 27 passing through the rear rail 11 to engage a fixing screw 281, a hollow screw 28 and a nut 29 so as to adjust the height of the sleeve means 27 relative to the rear rail 11. An orientation of the sleeve means 27 is adjustable from 10 to 15 degrees away from the central connecting portion 100 in the tolerance 23 defined by the clamping blocks 22.

A first threaded rod 14 passes through the first thread hole 21 of each guiding base 2. The guiding base 2 is slidable in the rear rail 11 so that the distance between the guiding bases 2 are adjustable by rotating the first width adjuster 141. Also, note that one of the first threaded holes 21 has a right-handed thread and the other has a left-handed thread.

Each positioning base 3 comprises a shaft 32, an elongation 33 encompassed by a spring 35 and adjacent to the shaft 32. The positioning arm 36 has a passage axially formed for the elongation 33 to pass through. A frontmost ends of the positioning arm 36 each has a toothed curvature 361 for engaging with respective toothed protuberances 371 of each rotatable means 37 so that the rotatable means 37 is engageable with the elongation 33 by a pin 38 passing through first pin holes 372 on the rotatable means 37 and a second pin hole 34 on the elongation 33. Combining in such a manner, each rotatable means 37 is detachable from the toothed curvature 361 of the positioning arm 36 by pressing the spring 35 so that the orientation of the rotatable means 37 is changeable.

A second threaded rod 18 passes through a second threaded hole 31 on each positioning base 3. The second width adjuster 181 is interposed in the second adjuster receiving means 16 so that a distance between each positioning base 3 is adjustable by rotating the second width adjuster 181 since one of the second threaded hole 31 has a right-handed thread, and the other has a left-handed thread.

Figure 5:
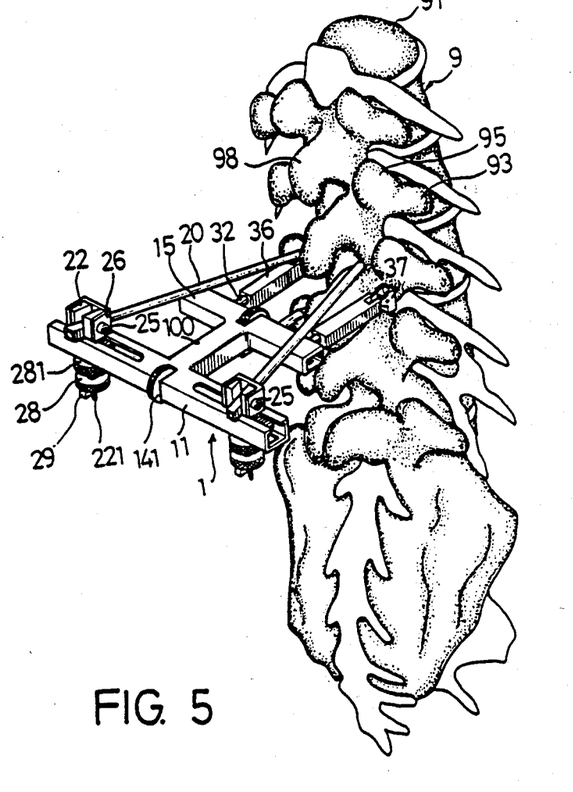
FIG. 5 is a perspective view of the spinal transpedicle drill jig of FIG. 3 in working state.

Referring to FIG. 5, the spinal transpedicle drill jig of the first embodiment in working state can be seen. The orientation of the rotatable means 37 is pre-settable according to the angle between the end plate 91 and the lamina 96 measured from lat-view of x-graph. In order to adjust the orientation, the positioning arm 36 is firstly drawn back so that the rotatable means 37 is disengageable with the positioning arm 36 by pressing the spring 35. In the meantime, the teeth of the protuberance 371 detach from the toothed curvature 361 of the positioning arm 36 is that the rotatable means 37 is adjustable to pre-set orientation. The following procedure is to suitably adjust the distance between the positioning arms 36 according to the width of specific vertebral body, by rotating the second width adjuster 181. The rotatable means 37 then are fixed against each lamina 96 so that the orientation, the width and the height of the sleeve means 27 are adjustable by moving the sleeve means 27 in the tolerance 23, by rotating the first width adjuster 141 and by loosening or tightening the hollow screw 28, respectively. Generally speaking, in the transverse plan the average angle measured from the thoracic spine between the central axis of the pedicle and the central axis of the vertebral bodies is approximately 10 degrees and measured from the lumbar spine is approximately 15 degrees. Therefore, the tolerance 23 permits the sleeve means 27 to adjusted from 10 to 15 degrees therein so that the guiding sleeve 20 is optionally settable in desired position.

Figure 6:
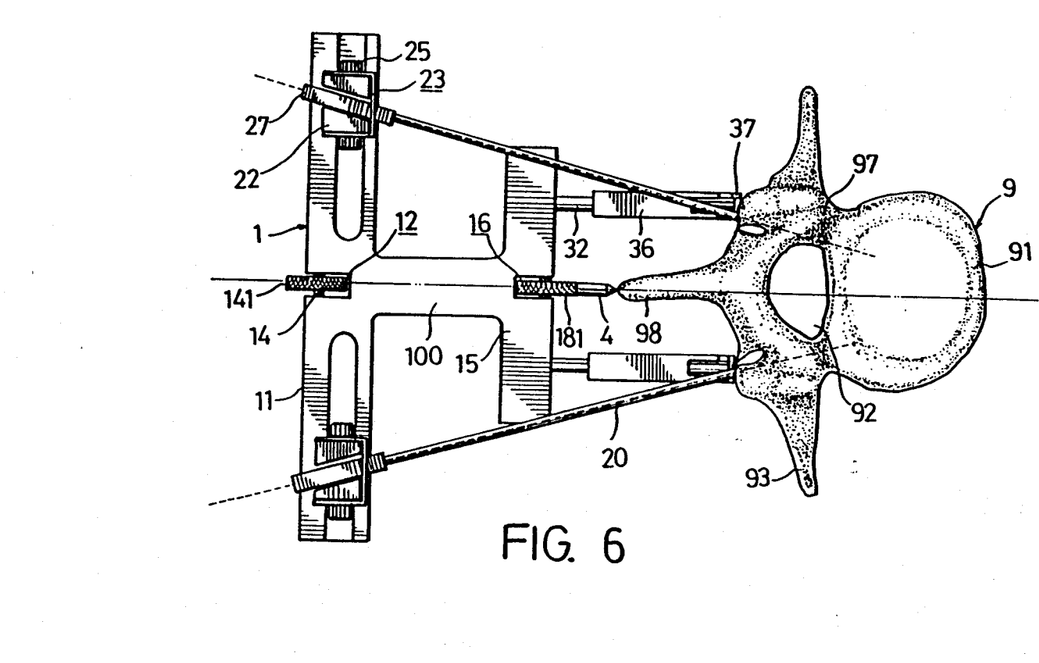
FIG. 6 is a top plan view of the spinal transpedicle drill jig of FIG. 5.
Figure 7:
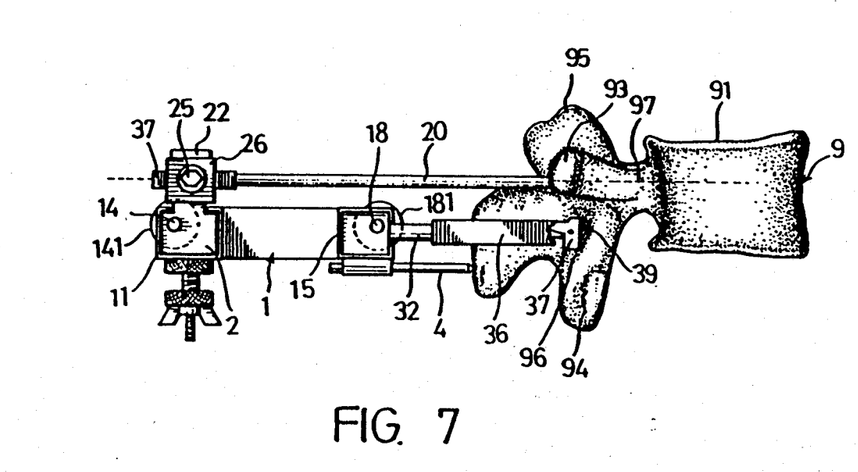
FIG. 7 is a side elevational view of FIG. 5.

As can be seen in FIGS. 6 and 7, in operation, the rotatable means 37 are against the lamina 96, then a needle 4 formed under the central connecting portion 100 is against the spinal process 98 to prevent the jig from slipping away in the manner that the guiding sleeves 20 are fixable on the suitable position, thereby permitting a guide pin to pass therethrough. It is preferred that the direction of drilling is set to be parallel with the end plate 91 and it is a safe route.

The exact angle between the axis of the pedicle and the central axis of the specific vertebral body in the transverse plane can be measured from computer tomogram scan pre-operation. Therefore, the guiding base 2 is pre-settable to facilitate drilling. With an accompanying fluoroscope to check the relative position of the transpedicle screw and the end plate 91 in operation, it is plausible to re-drill, if the transpedicle screw is in an unsuitable position.

Figure 8:
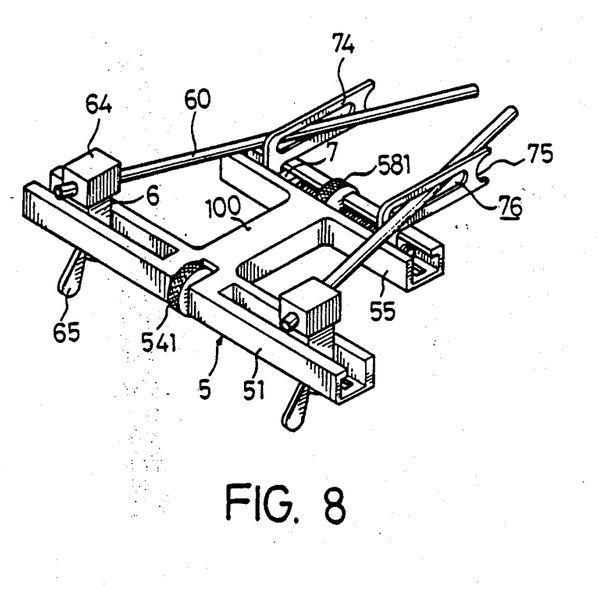
FIG. 8 is a perspective view of a second embodiment of a spinal transpedicle drill jig in accordance with the present invention.

A second embodiment of the spinal transpedicle drill jig according to the present invention is shown in FIGS. 8-11. The two embodiments of the present invention have the same function of defining a precise passage for the transpedicle screw. However, in the second embodiment, the different part of the construction is the form of the positioning bases so that positioning arms thereof are placed against the transverse process. With reference to FIG. 8, the spinal transpedicle drill jig for drilling holes on the pedicles, comprises an I-shaped body 5, a pair of guiding bases 6, and a pair of positioning bases 7.

Figure 9:
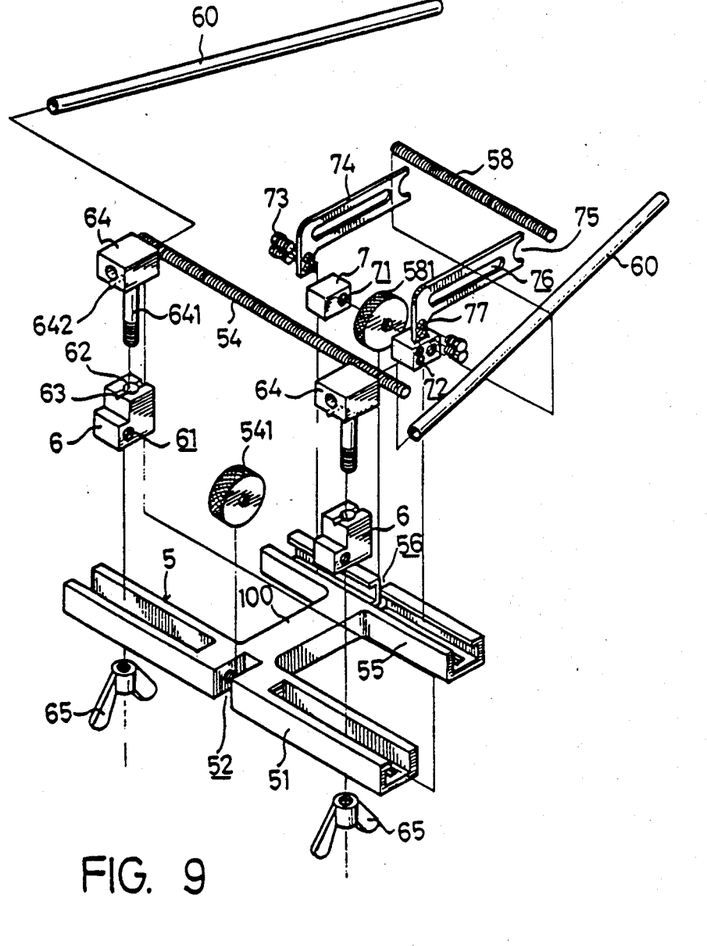
FIG. 9 is an exploded view of the spinal transpedicle drill jig of FIG. 8.

The I-shaped body 5 has a pair of front rails 55 and a pair of rear rails 51, the rear rails 51 and the front rails 55 being symmetrical about a central connecting portion 100. A first adjuster receiving means 52 is provided between each rear rail 51 for receiving a first width adjuster 541, and a second adjuster receiving means 56 is provided between each front rail 51 for receiving a second width adjuster 581.

A respective guiding base 6, which is substantially L-shaped, is slidable and securable in the rear rail 51 respectively and engageable with a respective sleeve means 64 integral with a threaded end 641. A first hole 61 is formed on the guiding base 6 for a first threaded rod 54 passing through and adjacent with two opposite grooves 63 thereon for engagement with a tip 642 protruding from the bottom of the sleeve means 64 so as to prevent relative motion therebetween. Each sleeve means 64 and corresponding threaded end 641 is adapted to receive one end of a guiding sleeve 60 and secure the guiding sleeve 60 thereon so that a height of the sleeve means 64 relative to the rear rail 51 is adjustable by the threaded end 641 which passes through the slot of the rear rail 51 to engage with a nut 65.

The positioning bases 7 are slidable and securable in respective front rail 55 and engageable with a respective positioning arm 74 which has an arched cutout 75 and a cam slot 76 thereon by means of coupled screw-ways 72, coupled holed 77 and coupled nuts 73. A first threaded rod 54 passes through the first threaded hole 61 of each guiding base 6. The guiding base 6 is slidable in the rear rail 51 so that the distance between the guiding bases 6 is adjustable by rotating the first width adjuster 541. Also, note that one of the first threaded holes 61 has right-handed thread; the other has a left-handed thread.

A second threaded rod 58 passes through a second threaded hole 71 on each positioning base 7 slidable in each front rail 55 and the second width adjuster 581 is disposed in the second adjuster receiving means 56 so that a distance between each positioning base 7 is adjustable by rotating the second width adjuster 581. Again, it can be seen that one of the second threaded holes 71 has a right-handed thread, the other has a left-handed thread.

Since one of the grooves 63 is at an angle of 10 degrees from the central connecting portion 100 and the other groove 63 is 15 degrees from the central connecting portion 100, the orientation of the sleeve means 64 is adjustable from 10 to 15 degrees by engaging the tips 641 with the two grooves 63 alternatively.

Figure 10:
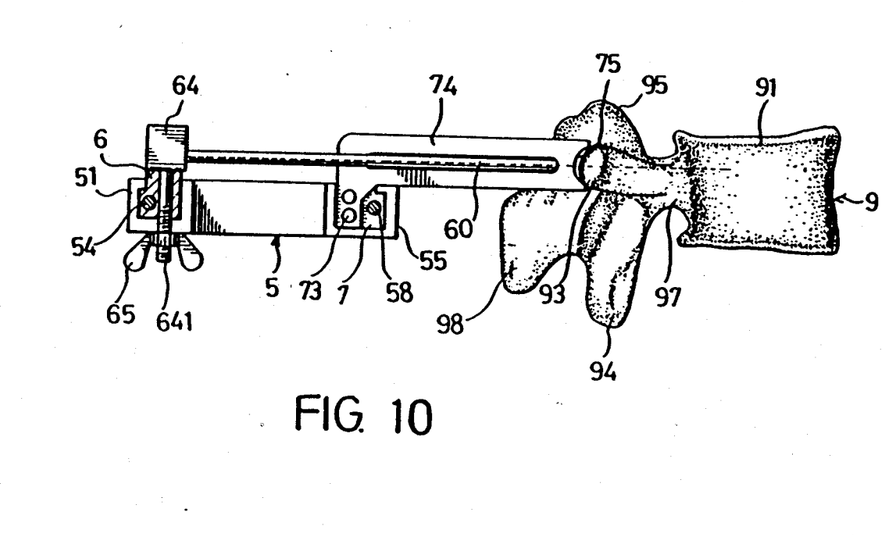
FIG. 10 is a side elevational view of the spinal transpedicle drill jig of FIG. 8 in working state.
Figure 11:
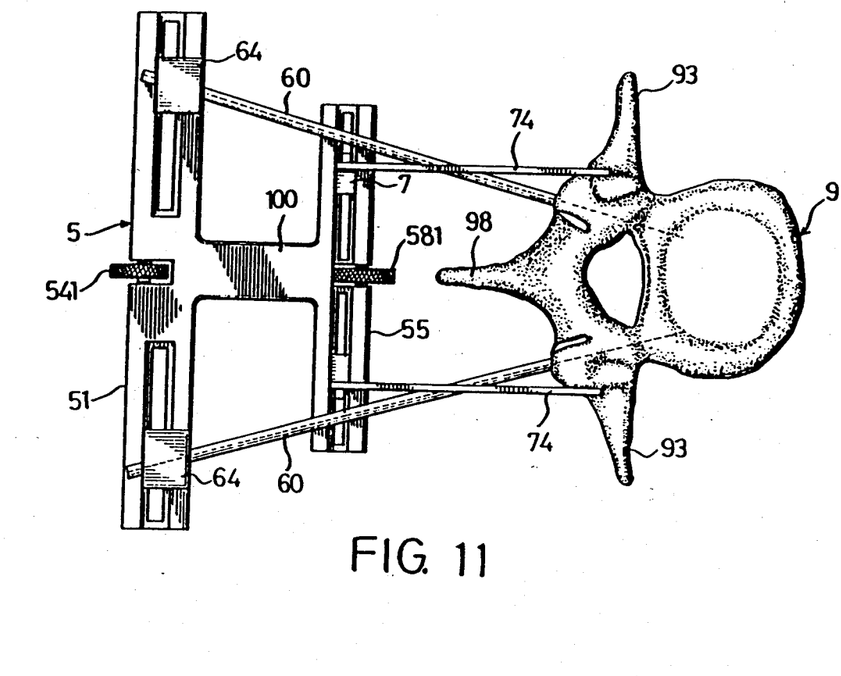
FIG. 11 is a top plan view of FIG. 10.

Further referring to FIGS. 10 and 11, the second embodiment of the spinal transpedicle drill jig according to the present invention in working state can be seen. During an operation, the arched cutouts 75 of the positioning arms 74 are fitted against the transverse process 93 and the guiding sleeves 60 are adjusted in the cam slots 76 of the positioning arms respectively further to stabilize the present invention against the vertebral body 9 for drilling. Of course, the second embodiment can achieve the same purpose as the first embodiment. For safer drilling, the spinal transpedicle drill jig can be used in conjunction with computer tomography and a fluoroscope.

While the present invention has been explained in relation to its preferred embodiments, it is to be understood that various modifications thereof will be apparent to those skilled in the art upon reading this specification. Therefore, it is to be understood that the invention disclosed herein is intended to cover all such modifications as fall within the scope of the appended claims.

I claim:

1. A spinal transpedicle drill jig comprising an I-shaped body, a pair of guiding bases and a pair of positioning bases;

said I-shaped body having a pair of front rails and a pair of rear rails; said rear rails and said front rails being respectively symmetrical about a central connecting portion; a first adjuster receiving means being provided between each said rear rail for receiving a first width adjuster; a second adjuster receiving means being provided between each said front rail for receiving a second width adjuster;

each said guiding base being slidable and securable in respective said rear rail and engageable with a respective sleeve means;

each said positioning base being slidable and securable in respective said front rail and engageable with a respective positioning arm.

2. A spinal transpedicle drill jig as claimed in claim 1, wherein each of said pair of guiding bases has two clamping blocks at an upper end thereof and a threaded hole extending lengthwise through a lower end thereof;

each of said clamping blocks being threaded; a respective U-shaped plate with an opening formed thereon being adjacent to each said clamping block; each said sleeve means receiving guiding sleeve and securing said guiding sleeve on said rear rail by means of a threaded end of said sleeve means passing through said rail to engage with a hollow screw so as to adjust a height of said sleeve means.

3. A spinal transpedicle drill jig as claimed in claim 2, wherein a first threaded rod passes through said first threaded hole of each said guiding base settable in said rear rail so that a distance between said guiding bases is adjustable by rotating said first width adjuster.

4. A spinal transpedicle drill jig as claimed in claim 2, wherein an orientation of said sleeve means is adjustable from 10 to 15 degrees from said central connecting portion between said clamping blocks.

5. A spinal transpedicle drill jig as claimed in claim 7, wherein a first threaded rod passes through said first threaded hole of each said guiding base, said guiding base being slidable in said rear rail so that a distance between each said guiding base is adjustable by rotating said first width adjuster.

6. A spinal transpedicle drill jig as claimed in claim 4, wherein the orientation of said sleeve means is adjustable from 10 to 15 degrees.

7. A spinal transpedicle drill jig as claimed in claim 5, wherein a second threaded rod passes through a second threaded hole on each said positioning base; a respective said positioning base being slidable in each said front rail and said second width adjuster being disposed in said second adjuster receiving means so that a distance between said positioning bases is adjustable by rotating said second width adjuster.

8. A spinal transpedicle drill jig as claimed in claim 1, wherein each said positioning base comprises a shaft, an elongation encompassed by a spring, said positioning arm, a rotatable means on a distal end of said positioning arm; a frontmost end of said positioning arm having a toothed curvature for engaging with teeth shaped on a protuberance of each said rotatable means; each said rotatable means being detachable from said toothed curvature of said positioning arm by pressing said spring so that an orientation of said rotatable means is adjustable.

9. A spinal transpedicle drill as claimed in claim 8, wherein a second threaded rod passes through a second threaded hole on each said positioning base; said second width adjuster being disposed in said second adjuster receiving means so that a distance between each said positioning base is adjustable by rotating said second width adjuster.

10. A spinal transpedicle drill jig as claimed in claim 1, wherein a needle is attached to a bottom of said central connecting portion.

11. A spinal transpedicle drill jig as claimed in claim 1, wherein a first hole is formed through each said guiding base, each guiding base being substantially L-shaped and having two opposite grooves thereon for engagement with a tip formed thereunder so as to prevent relative motion therebetween; each said sleeve means adjacent to a threaded end being adapted to receive one end of a guiding sleeve and secure said guiding sleeve thereon so that a height of said sleeve means is adjustable.

12. A spinal transpedicle drill jig as claimed in claim 1, wherein each said positioning base is engageable with a respective said positioning arm, each positioning arm having an arched cutout and a cam slot thereon; said cam slot being provided for securely receiving said guiding sleeve therein.

* * * * *